United States Patent
Xie et al.

(10) Patent No.: US 11,191,522 B2
(45) Date of Patent: Dec. 7, 2021

(54) ULTRASOUND SHEAR WAVE ELASTOGRAPHY FEATURING THERAPY MONITORING

(71) Applicant: KONINKLIJKE PHILIPS N.V., Eindhoven (NL)

(72) Inventors: Hua Xie, Cambridge, MA (US); Shiwei Zhou, Yorktown Heights, NY (US); Jean-luc Robert, Cambridge, MA (US); Vijay Thakur Shamdasani, Kenmore, WA (US); Sheng-Wen Huang, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 489 days.

(21) Appl. No.: 15/320,570

(22) PCT Filed: Jun. 15, 2015

(86) PCT No.: PCT/IB2015/054498
§ 371 (c)(1),
(2) Date: Dec. 20, 2016

(87) PCT Pub. No.: WO2016/001783
PCT Pub. Date: Jan. 7, 2016

(65) Prior Publication Data
US 2017/0188997 A1    Jul. 6, 2017

Related U.S. Application Data

(60) Provisional application No. 62/019,030, filed on Jun. 30, 2014.

(51) Int. Cl.
A61B 8/08    (2006.01)
A61B 8/00    (2006.01)
(Continued)

(52) U.S. Cl.
CPC .............. *A61B 8/485* (2013.01); *A61B 8/085* (2013.01); *A61B 8/465* (2013.01); *A61B 8/54* (2013.01);
(Continued)

(58) Field of Classification Search
None
See application file for complete search history.

(56) References Cited

U.S. PATENT DOCUMENTS 8,715,187 B2 * 5/2014 Landberg Davis ...... A61N 7/02
600/439
8,961,418 B2 * 2/2015 Fan ........................ A61B 8/485
600/438

(Continued)

OTHER PUBLICATIONS

Lizzi, et al., "Radiation-Force Technique to Monitor Lesions During Ultrasonic Therapy", Ultrasound in Med. & Biol, vol. 29, No. 11, 2003, pp. 1593-1605.

(Continued)

*Primary Examiner* — Christopher Koharski
*Assistant Examiner* — Younhee Choi (57) ABSTRACT

An ultrasound exposure safety processor is configured for spatially relating respective definitions of an imaging zone, and an extended dead-tissue zone that includes both a dead-tissue zone and a surrounding margin. Based on whether a push pulse focus is to be within the extended dead-tissue zone, the processor automatically decides a level of acoustic power with which the pulse is to be produced. If the pulse focus is to be within the extended dead-tissue zone, the pulse may be produced with a mechanical index (MI), a thermal index (TI), and/or a spatial-peak-temporal-average intensity (IspTA) that exceeds respectively 1.9, 6.0 and 720 milliwatts per square centimeter. The imaging zone may be definable interactively to dynamically trigger the deciding and the producing, with push pulse settings being dynami-
(Continued)

cally derived automatically. A display of multiple push pulse sites allows user manipulation of spatial definition indicia to dynamically control displacement tracking.

14 Claims, 4 Drawing Sheets

(51) Int. Cl.
 A61B 18/14 (2006.01)
 A61B 18/00 (2006.01)
(52) U.S. Cl.
 CPC ...... *A61B 18/14* (2013.01); *A61B 2018/0066* (2013.01); *A61B 2018/00351* (2013.01); *A61B 2018/00529* (2013.01); *A61B 2018/00547* (2013.01); *A61B 2018/00577* (2013.01); *A61B 2018/00738* (2013.01); *A61B 2018/00994* (2013.01)

(56) References Cited

U.S. PATENT DOCUMENTS

| | | | |
|---|---|---|---|
| 2005/0215899 A1* | 9/2005 | Trahey | A61B 5/0048 600/439 |
| 2010/0016719 A1* | 1/2010 | Freiburger | A61B 8/00 600/443 |
| 2012/0302883 A1* | 11/2012 | Kong | A61N 7/02 600/439 |
| 2014/0105474 A1* | 4/2014 | Lee | G06T 7/0012 382/128 |

OTHER PUBLICATIONS

Fahey, et al., "Acoustic Radiation Force Impulse Imaging of Myocardial Radiofrequency Ablation: Initial in Vivo Results", IEEE Transactions of Ultrasonics, Ferroelectrics, and Frequency Control, vol. 52, No. 4, Apr. 2005, pp. 631-641.

* cited by examiner

ULTRASOUND SHEAR WAVE ELASTOGRAPHY FEATURING THERAPY MONITORING

This application is the U.S. National Phase application under 35 U.S.C. §371 of International Application No. PCT/IB2015/054498, filed on Jun. 15, 2015, which claims the benefit of U.S. Provisional Application Ser. No. 62/019,030, filed Jun. 30, 2014. These applications are hereby incorporated by reference herein.

FIELD OF THE INVENTION

The present invention relates to medical ultrasound push pulse generation and, more specifically, to applications that involve dead body-tissue.

BACKGROUND OF THE INVENTION

Radio-frequency ablation (RFA) is gaining widespread use in minimally invasive treatment of unresectable malignant hepatic tumors. The clinical problem associated with RFA procedures is the high local recurrence rate in treated patients: ranging from 1.7% to 41% for hepatocellular carcinoma. A primary reason is that inaccurate identification of the ablation zone, especially errors in size measurement, leads to undertreatment. The standard of success by which ablation is currently measured is complete destruction of all malignant cells along with a safe margin of normal tissue. It is therefore important for physicians to be able to identify the ablation region and assess therapy success while the patient is still in surgery. A variety of imaging modalities have been attempted to visualize the ablation zone including conventional B-mode ultrasound (US), contrast-enhanced US (CEUS), contrast-enhanced computed tomography (CT), magnetic resonance imaging (MRI) and positron emission tomography (PET). All of these modalities are of limited use, because they carry certain disadvantages. Specifically, US does not provide adequate brightness contrast between ablated and surrounding tissue; the use of CEUS for liver imaging has not been approved by Food and Drug Administration (FDA), and the other modalities lack the capability of real-time evaluation and dynamic monitoring of the effects of therapy. The above drawbacks likewise apply to other thermal based therapy options for treating a tumor, include high-intensity focused ultrasound (HIFU) and microwave ablation.

During RFA procedures tissue stiffness is elevated due to thermal necrosis. The high stiffness contrast between treated and non-treated tissue has led to the development and use of ultrasound elastography for visualizing the coagulation zone during liver RFA. Acoustic radiation force based ultrasound shear wave elastography has been proposed to monitor and assess the ablation region for therapy guidance by quantitatively measuring tissue mechanical properties such as shear modulus (or the similar "Young's modulus") and shear viscosity.

In acoustic radiation force based ultrasound shear wave elastography, the dedicated pulse sequence consists of one or more long push pulses (typically hundreds of microseconds long each) and a series of interleaved tracking pulses. Due to the effect of acoustic radiation force, the push pulse causes tissue in the focal area to move away from the probe surface, simultaneously establishing a shear wave propagating away from the focal region in a direction perpendicular to the push beam.

For each lateral position along the shear wave pathway at the focal depth, the tissue motion induced by the shear wave will be mainly in the same direction as the push beam. Consequently, the tracking pulses can monitor such dynamic response for each position and derive, position-by-position, a displacement waveform representing the magnitude of tissue movement as a function of time.

By tracking displacements at multiple locations along the shear wave propagation path, one can estimate shear wave speed and further determine absolute values of tissue mechanical properties.

The speed at which a shear wave propagates inside tissue is governed, according to some mechanical models, by shear modulus, shear viscosity, tissue density and shear wave frequency.

The stiffer the tissue is, the faster the waves move—however with lower shear wave vibration amplitude.

In one study, ex vivo porcine liver stiffness was found to be significantly greater for those areas that had undergone RFA than areas not treated. See H. Xie, S. Zhou, J. Robert and V. Shamdasani, "Quantitative Assessment of Thermal Lesion Stiffness in the Liver: Initial ex vivo Results", 2011 IEEE International Ultrasonics Symposium Proceedings, pp. 2098-2011.

The study notes that a combination of factors, including shear wave displacement signal-to-noise ratio (SNR), collectively amount to an upper limit in the accuracy of shear elasticity estimation, and that the SNR is bounded by FDA thermal and mechanical index limits applied to diagnostic ultrasound imaging.

In another in vivo study of acoustic radiation force impulse (ARFI) imaging of the heart, ARFI-induced displacements were found to rise with transmit power level. See D. Bradway, P. Hollender, et. al, "Feasibility and Safety of Transthoracic Cardiac Acoustic Radiation Force Impulse Imaging Methods", 2012 IEEE International Ultrasonics Symposium Proceedings, pp.2027-2030.

This included emissions with a mechanical index (MI) exceeding the FDA exposure limit for diagnostic ultrasound imaging of 1.9, although heat dissipation from physiological motion, and blood perfusion, of the heart diminished any potential bioeffects from temperature rise.

SUMMARY OF THE INVENTION

What is proposed herein below addresses one or more of the above concerns. For the application of liver RFA visualization and assessment, it is important to delineate the ablation zone with high accuracy. During the procedure, the stiffness will increase to approximately, by either measure, i.e., Young's modulus or the shear modulus (in soft tissues Young's modulus is about 3 times shear modulus), 50-200 kilopascals (kPa), leading to significant reduction in shear wave amplitude and poor shear wave SNR. If the displacement drops below the level of ultrasound motion tracking accuracy (<1 µm), erroneous estimation, or even failure to yield a stiffness reading, will occur and result in inaccurate ablation zone visualization and potentially incomplete ablation treatment.

Visualizing and predicting the progress of a developing ablation region is important in guiding the therapy procedure and evaluating its effectiveness. To reliably distinguish surrounding non-treated normal tissue, the transition zone and the necrosis zone, shear wave elastography should have the capability of accurately and robustly quantifying a stiffness range from 5 kPa to potentially 200 kPa or even higher.

In accordance with what is proposed herein, incorporated into a diagnostic scanner is a specialized shear wave elastography feature. The feature can excite push pulses with higher driving voltage and/or longer push duration to enhance shear wave signal amplitude for targeted tumor ablation regions. Considering the invasive nature of liver RFA therapy, slightly exceeding diagnostic mechanical index (MI), thermal index (TI) and spatial-peak-temporal-average intensity ($I_{SPTA}$) safety limits should not pose the potential for more severe tissue damage than coagulation necrosis by thermal based therapy. Limited clinical trials have been carried out in vivo using shear wave elastography with acoustic output moderately elevated above the regulatory limits, just for diagnostic imaging purposes. In one study, push pulses with mechanical indices of 1.9, 2.5 and 3.0 were used on volunteers. As anticipated, no clinical evidence of adverse events has been reported. The advantages of what is proposed herein for therapy monitoring include more accurate tissue stiffness quantification, more robust measurement, and better imaging reproducibility than the shear wave elastography feature currently designed for diagnostic imaging. To protect the patient's safety, multiple safety mechanisms are also proposed.

In one aspect of what is proposed herein, an ultrasound exposure safety processor is configured for spatially relating respective definitions of: a) an extended dead-tissue zone that includes both a dead-tissue zone and a surrounding margin; and b) an imaging zone. Based on whether a focus of a push pulse is to be within the extended dead-tissue zone, the processor automatically decides as to a level of acoustic power with which the pulse is to be produced, and causes the pulse to be produced with the decided upon level.

As a sub-aspect, the processor is configured for the producing, if the pulse focus is to be within the extended dead-tissue zone, with an MI, a TI, and/or an $I_{SPTA}$ that exceeds respectively 1.9, 6.0 and 720 milliwatts per square centimeter.

Details of the novel, therapy specific ultrasound shear-wave-elastography exposure-safety facility are set forth further below, with the aid of the following drawings, which are not drawn to scale.

DETAILED DESCRIPTION OF EMBODIMENTS

Figure 1:
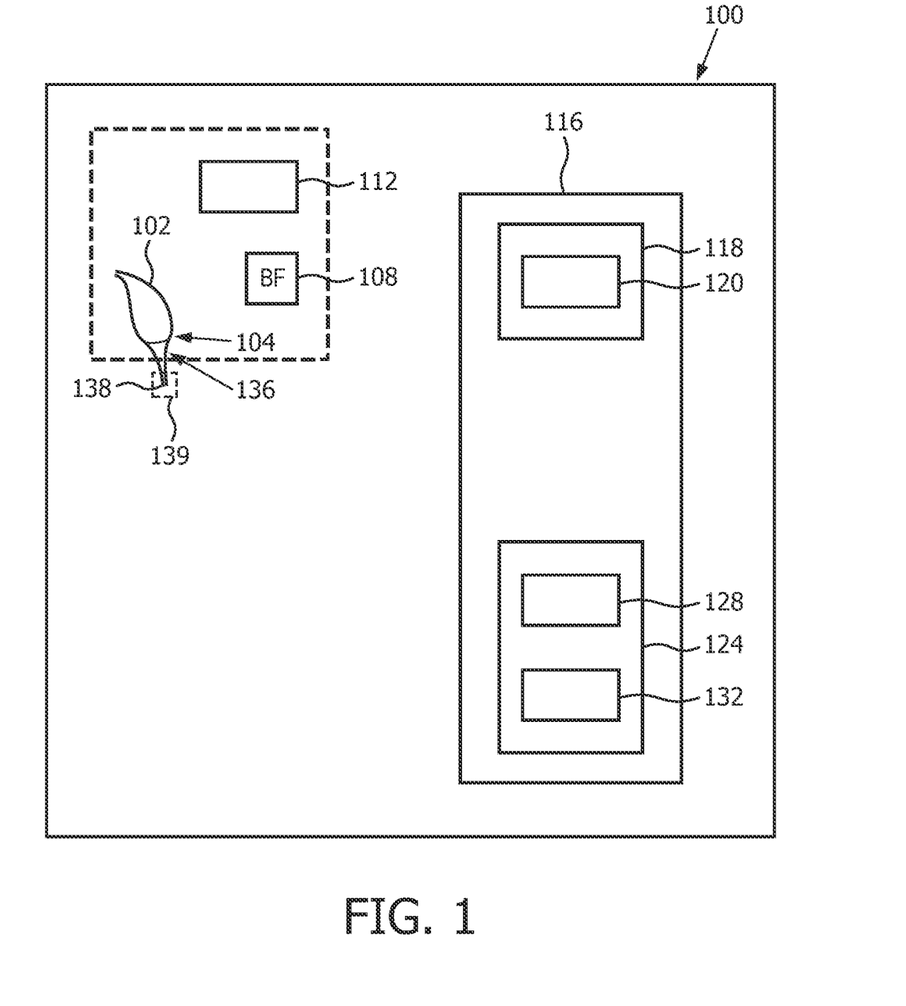
FIG. 1 is a schematic diagram of one example of a system that features a therapy specific ultrasound shear-wave-elastography exposure-safety facility, in accordance with the present invention.

FIG. 1 depicts, by way of illustrative and non-limitative example, an ultrasound scanner 100 which incorporates a therapy specific ultrasound shear-wave-elastography exposure-safety facility. In effect, the facility is implementable on a conventional diagnostic ultrasound system. The scanner 100 includes an ultrasound imaging probe 102 that incorporates an ultrasound transducer 104, an ultrasound beamformer 108, an ultrasound exposure safety processor 112, and a user interface 116. The user interface 116 includes a display 118 having a screen 120, and a user control section 124 that includes a facility enablement switch 128 and a fingerprint scanner 132.

The transducer 104 is configured for conventional ultrasound imaging modes, e.g., A-mode, two-dimensional (or "B-mode") imaging, Doppler, contrast imaging and etc. It is further configured for producing, i.e., forming and emitting, acoustic-radiation-force-based push pulses 136 for shear wave elastography imaging. Alternatively, separate transducers may be provided. For example, one can be designed for generating the push pulses 136 with foci 138. The other can be designed for generating tracking pulses along multiple beam directions, and for the B-mode imaging. The two types of transducer may be concentically arranged. A dot 139 appears as a broken line in FIG. 1, and, as discussed further herein below, corresponds to an onscreen displayed symbol representative of the site of the focus 138.

Activation of the facility may be accomplished via the fingerprint scanner 132, as a safety measure. Alternatively, or in addition, it may be required that a password be entered.

The facility enablement switch 128, and its arrangement in the user control section 124, constitute an additional safety measure.

Figure 2:
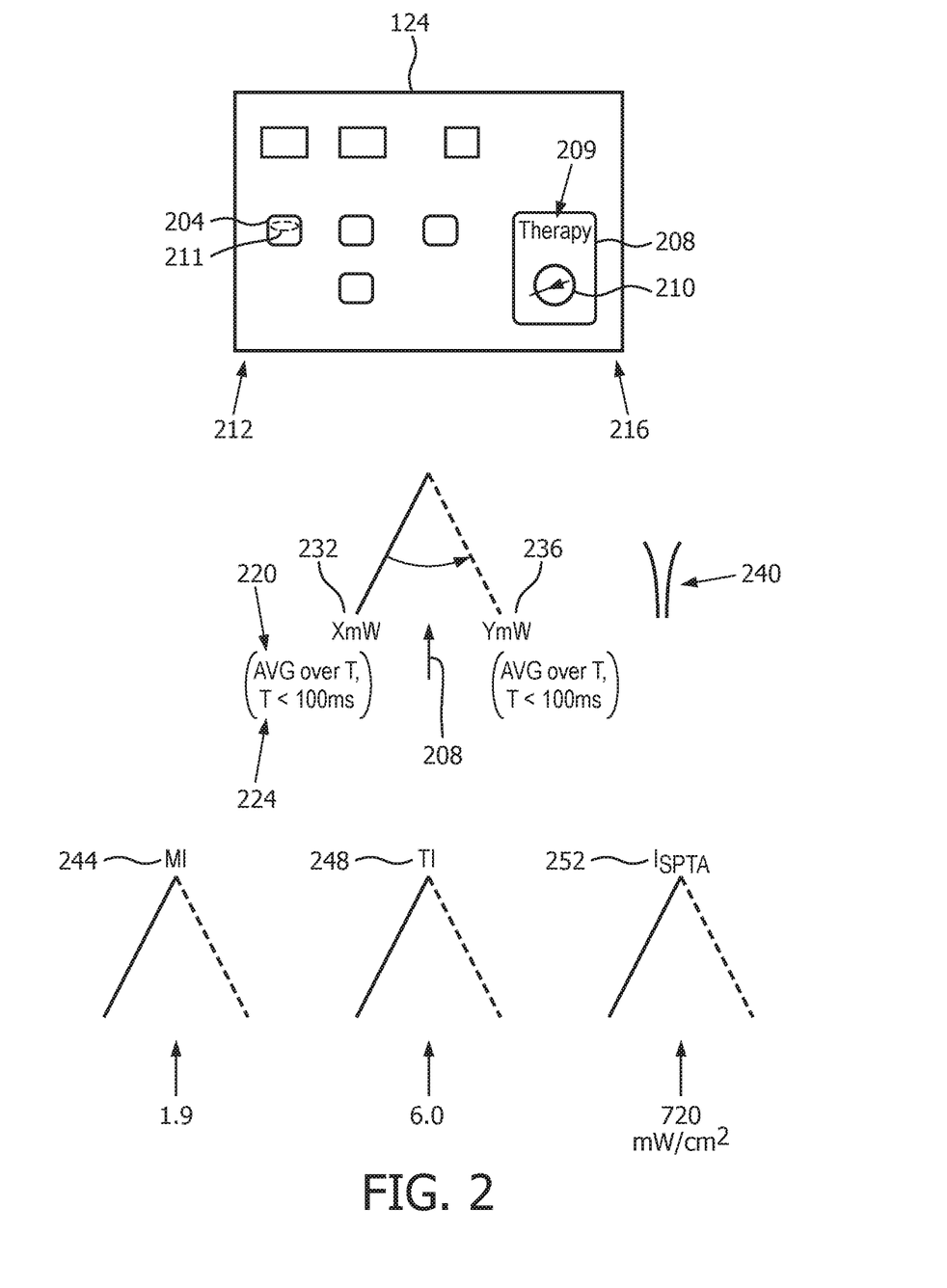
FIG. 2 is a conceptual and schematic diagram exemplary of user controls and irradiation levels, in accordance with the present invention.

Referring to FIG. 2 which constitutes an example scenario, the user control section 124 includes multiple user-actuatable buttons. The user control section 124 may be a system touch panel, keyboard, or part of the display screen 120. The buttons may be mechanical buttons or soft buttons on the display screen 120. More generally, they may be any types of user-actuatable switches or other controls. Two of the buttons are specialized for activating respective modes of operation that both involve producing ultrasound push pulses, as in shear wave elastography applications. One of the modes may by a typical diagnostic mode for shear wave elastography. The other mode, the "therapy mode", is specific to the exposure-safety facility. The two buttons 204, 208 are disposed at opposite ends 212, 216 of the control section 124. The diagnostic mode button 204 is colored green; whereas, the therapy mode button 208 for the exposure-safety facility is colored red. Also, the therapy mode button 208 has a label 209, icon 210 such as a cartoon, or both, representative of therapy. A cartoon, for example, may show the the multiple tips of an RFA electrode. By contrast, the diagnostic mode button 204 has no such label or icon. In the current example, the diagnostic mode button is provided with a visible label 211 representative of diagnostic imaging, such as "diagnosis." The therapy mode button 208 is, in addition, considerably larger than the diagnostic mode button 204. Due to the above-described design of the two buttons 204, 208, an operator is unlikely to inadvertently press one of the two buttons when the other one was intended. Moreover, even if the therapy mode button 208 were to be pressed in error, the operator would then be prompted for password or biometric activation of the exposure-safety facility.

In therapy mode for the example scenario of FIG. 2, push pulses 136 emitted to a region being treated are produced with an acoustic power that slightly exceeds FDA exposure limits for diagnostic ultrasound imaging. The larger acoustic power results in larger body tissue displacements and consequently greater SNR. Advantageously, what allows for this slight departure from FDA diagnostic safety standards is the fact that the push pulse 136 is placed at a site of thermal ablation, and any possible bioeffects of the push pulse, mainly thermal, would not negatively impact that site.

Acoustic power varies with a number of factors, such as pulse duration, transmit voltage and aperture size. Acoustic power can be assessed as an average acoustic power 220 over a predetermined time period 224, less than 100 milliseconds for example. Acoustic power 220 beyond a predetermined power threshold 228 for a push pulse 136 is only enabled in therapy mode, and only if the focus 138 of the pulse in within the extended dead-tissue zone. The latter is a zone within the body tissue that includes a dead-tissue zone, such as an ablation zone, and a surrounding margin that can be planned and defined by the physician. The margin, which is at least partially surrounding, serves as a transition between normal, untreated tissue and the ablation zone. An acoustic power 232 of X milliwatts (mW), which is equal to or below the threshold 228, might not, and at least typically would not, be used in therapy mode in the extended dead-tissue zone; whereas, an acoustic power 236 of Y mW which exceeds the threshold can only be produced in therapy mode and only if the focus 138 of the pulse 136 is in the extended dead-tissue zone. More particularly, by default, if not always, therapy mode push pulses 136 whose foci 138 are in the extended dead-tissue zone are produced with an acoustic power that exceeds the threshold 228. Pulse 240 produced with acoustic power Y is, by virtue of the fact that Y exceeds the threshold 228, produced with at least one of a mechanical index (MI) 244, a thermal index (TI) 248, and a spatial-peak-temporal-average intensity ($I_{SPTA}$) 252 exceeding respectively 1.9, 6.0 and 720 milliwatts per square centimeter. Although pulses 136 can be produced with two levels of acoustic power, they can alternatively be produced with multiple levels. For example, the relatively high-powered pulse 240 may be produced with one level of acoustic power when focused in the dead-tissue zone and with another, possibly lower, level when focused in the margin, albeit at a level that still exceeds the power threshold 228.

Figure 3A:
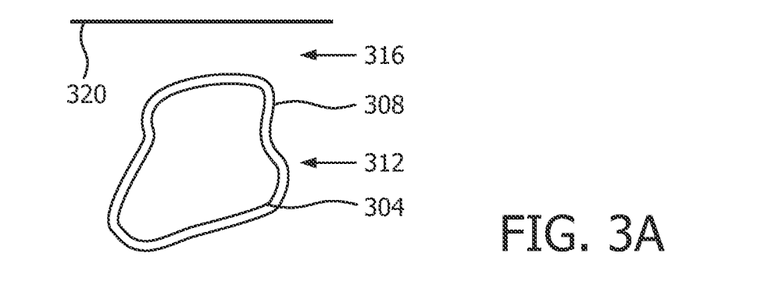
FIGS. 3A, 3B, 3C, and 3D are conceptual and schematic diagrams of possible screens and possible body tissue regions, in accordance with the present invention.

FIG. 3A shows a dead-tissue zone 304 in which ablation occurs, surrounded by a margin 308. The zone 304 and its margin 308 collectively are referred to as an "extended dead-tissue zone" 312. The latter exists within body tissue 316 under skin 320 of a human or animal patient or within an ex vivo sample. The dead-tissue zone 304 may correspond to, or include, a tumor treated by ablation, such as RFA, HIFU and microwave ablation.

Like the two zones 304, 312 above, an elastography imaging zone is defined in a preliminary step in the therapy mode. It is within the imaging zone (illustrated in the examples below) where the foci 138 of therapy mode push pulses 136 are located; although, it is noted that a push pulse may be partially, or even totally albeit slightly, outside the imaging zone, and depicted as such by the placement of its corresponding symbol onscreen.. In particular, an imaging zone exists, like the foci 138, within body tissue. Some of the foci 138 are outside the extended dead-tissue zone 312, so that stiffness readings from inside the zone can be compared to those from outside so as to localize a current border of the zone. The border between the margin 308 and the dead-tissue zone 304 is also monitored.

Although ablation, in the examples discussed herein, is the cause of death of the tissue in the dead-tissue zone 304, the intended scope of what is discussed herein is not limited to ablation. The cause of death may, for instance, be natural. In some of such cases, the slightly elevated power level of ultrasound exposure would not have any negative impact. In this scenario, elastography, shear wave or otherwise, may be performed for purposes other than determining borders. Such purposes may include staging, or fibrosis quantification, before surgery.

Figure 3B:
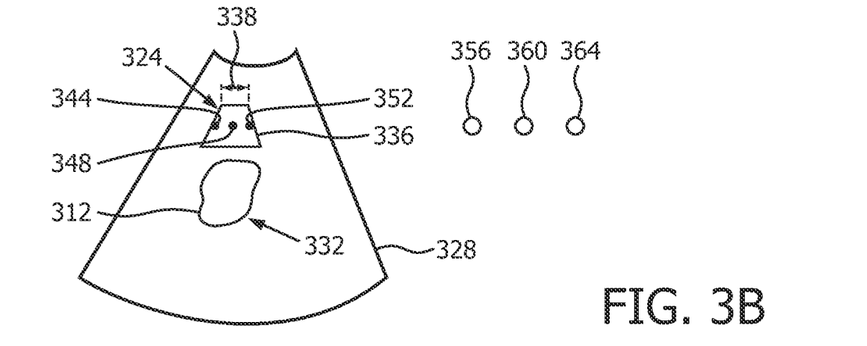
Figure 3C:
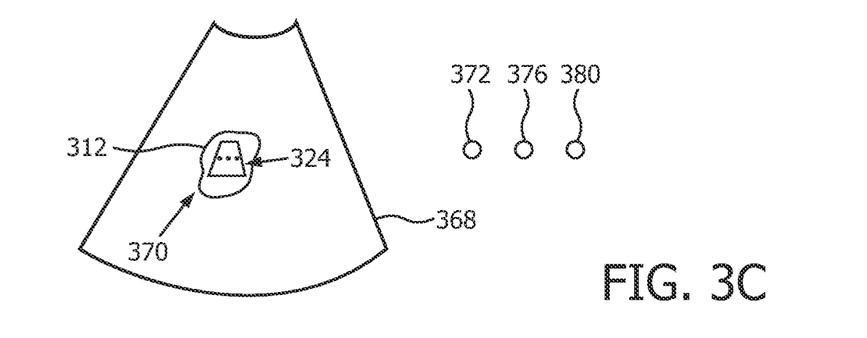
Figure 3D:
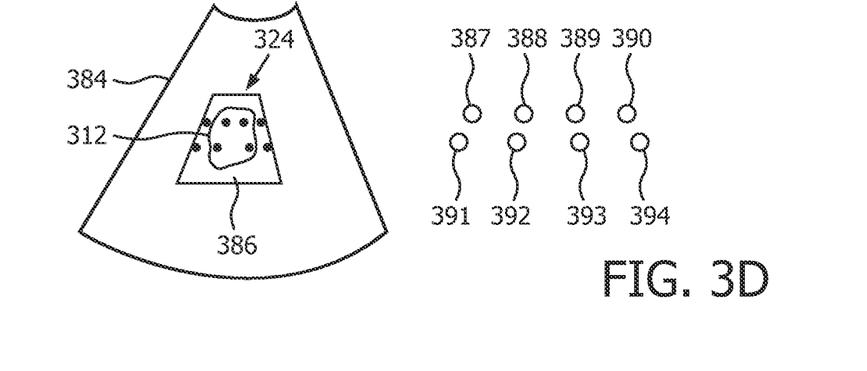

At least both the extended dead-tissue zone 312 and the imaging zone are depicted on the screen 120 of the display 118. A few examples reflecting particular user interactions are seen in FIGS. 3B, 3C, and 3D. B-mode images are shown, adhering to the convention that the fan-out narrows toward the top of the depiction, leading toward where the imaging probe 102 is located.

In FIG. 3B, over a B-mode image 328, a definition 332 of the extended dead-tissue zone 312 is shown. An elastography imaging box 336 has a span 338 which is matched against a criterion in launching the push pulses 136 and intervening body-tissue displacement tracking, as discussed further below. The imaging box 336, a screen graphic, corresponds to an imaging zone 324 which exists within body tissue. In the current example, it can be seen that the imaging zone 324 is disjoint from or non-overlapping 340 with the extended dead-tissue zone 312. Accordingly, no relatively high power pulse 136 such as the above-mentioned pulse 240 issues. Thus, the three pulse focus sites 344, 348, 352, appropriately are in the imaging zone 324 and are, as ordinarily would be this case, not in the extended dead-tissue zone 312. The three sites 344-352 are accordingly green, indicating that the respective pulses 136 are produced with a lower, diagnostic-mode type of acoustic power 232 such as that decided upon for a pulse 136 whose focus 138 is not within the extended dead-tissue zone 312. The three pulse focus sites 344-352 are depicted onscreen, overlaid onto the B-mode image 328, as symbols 356, 360, 364, such as dots.

For a second B-mode image 368 seen in FIG. 3C, the two zones 312, 324 overlap 370 The three dots 372, 376, 380 are red, since they are seen onscreen as superimposed on and therefore "in" the extended dead-tissue zone 312, implying that the respective pulse sites correspond to pulses 136 whose foci 138 are within the extended dead-tissue zone.

For a third B-mode image 384 as shown in FIG. 3D, the two zones 312, 324 again overlap. However, in perhaps a more typical scenario, the imaging zone 324 overextends the extended dead-tissue zone 312 to form a non-overlapping portion 386. Four of the dots 387, 390, 391 and 394 are green, and four of the dots 388, 389, 392 and 393 are red. The elastography imaging zone 324 can be extended to match any targeted extent of the B-mode image 384 underlying the superimposed graphics such as the imaging box 336. In FIGS. 3A-3D, the number of push foci 138 is selected just for illustration purposes. The actual number of push foci 138 in the lateral and axial directions is intelligently determined by the system depending on information of the push pulse acoustic characteritcs, underlying tissue properties and the size of the elastography imaging box 336. "Axial" is in the imaging depth direction of the ultrasound probe 102. "Lateral" is in the azimuthal direction. As discussed in more detail below, whenever dots 387-394 are seen onscreen and the imaging box 336 meets a sufficient-size criterion, body tissue displacement tracking is ongoing for the respective sites. The tracking can be serial, site by site, or in parallel, as via multiline acquisition. The tracking entails, for each site 344, firing tracking pulses repeatedly, at a pulse repetition frequency (PRF) such as 2 kilohertz (kHz).

Figure 4:
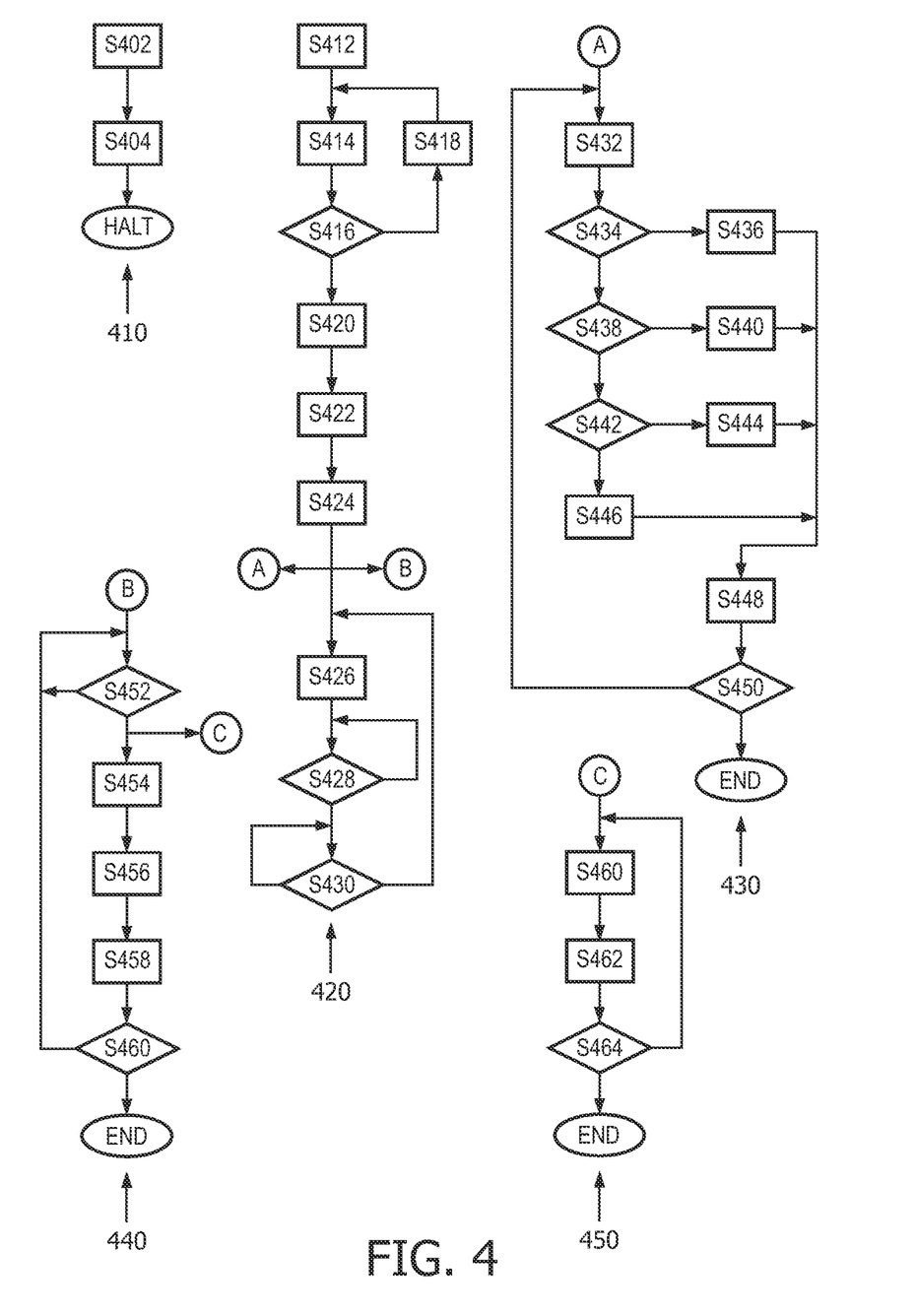
FIG. 4 consists of flow diagrams serving as examples of how the therapy specific ultrasound shear-wave-elastography exposure-safety facility operates.

Operationally and as seen in FIG. 4, in a diagnostic mode subprocedure 410, the green button 204 is pressed (step S402). A mode leading to push pulse operation is thereby enabled (step S404). Any firing of a push pulse 136 is with its acoustic power not exceeding the power threshold 228.

When, in a main subprocedure 420, the red button 208 is pressed (step S412). The user is prompted to enter a password or input a biometric identifier, as by swiping a finger over a fingerprint scanner (step S414). If the password/identifier is not accepted (step S416), the user is re-prompted (step S418) and return is made to step S414. The extended dead-tissue zone 312 is spatially defined (step S420). The definition 332 can be done either manually by the physician based on tumor appearance on real-time ultrasound imaging, or automatically by tumor segmentation through registering pre-surgery images captured by MRI, CT or other imaging modalities and real-time ultrasound images. In the first case, the system user interface will provide a simple tool to define shapes such as circle, ellipse, rectangle, square, and free-form polygons. Next, the ultrasound exposure safety processor 112 sets a box-span threshold $T_{BS}$, based on the size or an extent of the just-defined extended dead-tissue zone 312 (step S422). The larger the zone 312, the larger the span 338 of the imaging box 336 will tend to be. Launching and maintaining body-tissue displacement tracking is dependent of the span 338 being sufficiently large. The just-defined extended dead-tissue zone 312 is displayed on the screen 120 (step S424). At this point in the processing, a site visualizing subprocedure 430 and a displacement tracking subprocedure 440 are launched for concurrent execution with the next, i.e., imaging box manipulation, step of the instant subprocedure 420, with the displacement tracking subprocedure being "placed in a holding pattern" until the user sufficiently enlarges the imaging box 336. Next in the main subprocedure 420, the user control section 124 is utilized to manipulate (e.g., drag, expand, contract) the imaging box 336 based on location and size of the tumor in the B-mode image 328 and on what location is to be currently imaged by the tracking (step S426). The pulses 136 of a series may be focused on a particular site 344, or on a group 344-352 of sites, and may be repetitive over that group. Any push pulse site 344 added for the series by the manipulation of the imaging box 336 dynamically produces the pulses of the added site as part of the series. When it is detected, from the user control section 124, that the manipulation has ended (step S428) but has later resumed (step S430), return is made to the box manipulation step S426).

Concurrently with step S426 of the main subprocedure 420, the site visualizing subprocedure 430 visualizes the pulse sites 344. First, the ultrasound exposure safety processor 112 spatially relates the spatial definition 332 of the extended dead-tissue zone 312 to the spatial definition of the imaging zone 324 (step S432). The user may have provided the latter definition by the positions, and orientations, of the polygonal sides of the imaging box 336 or, in the case of a curved boundary, its position and, if applicable, orientation. With regard to the relating of the definitions and by way of example, if there is no overlap 370 between the imaging zone 324 and the extended dead-tissue zone 312 (step S434), then, extending adjacently to, rather than toward or away from, the extended dead-tissue zone 312, there is formed a single linear array of foci 138 to be produced with acoustic power not exceeding the power threshold 228, as seen herein above for the three pulse focus sites 344-352 (step S436). Otherwise, if there is overlap 370 (step S434), the processing choice depends on whether the imaging box 336 is fully within the extended dead-tissue zone 312 (step S438). If the imaging box 336 is fully within the extended dead-tissue zone 312 (step S438), then, within the extended dead-tissue zone 312, there is formed a single linear array of foci 138 to be produced with acoustic power 236 that exceeds the power threshold 228 (step S440). If, on the other hand, the imaging box 336 is not fully within the extended dead-tissue zone 312 (step S438), the processing choice depends on whether the extended dead-tissue zone 312 is fully within the imaging box 336 (step S442). If the extended dead-tissue zone 312 is fully within the imaging box 336 (step S442), then, within the imaging box 336, a planar array of foci 138 in the axial and lateral directions is formed (step S444). Push pulses with foci 138 in the extended dead-tissue zone 312 are to be produced with acoustic power 236 that exceeds the power threshold 228. Push pulses 136 with foci 138 not in the extended dead-tissue zone 312 are to be produced with acoustic power 232 that does not exceed the power threshold 228. An amount, or amounts, by which the imaging box 336 overextends the extended dead-tissue zone 312 can be taken into account. The automatic push pulse setting can, for example, create one or more push pulses outside the extended dead-tissue zone 312 in correspondence with the determined amount, or amounts, of overextension. On the other hand, if the extended dead-tissue zone 312 is not fully within the imaging box 336 (step S442), other relation-based rules are applicable (step S446). For example, a partial overlap implies higher-powered pulses in the overlap portion and lower-powered pulses in the remaining imaging box portion. This approach could be potentially used iteratively in ablating the entire tumor. In any event, regardless of the relation, symbols at the sites 344 of the respective foci 138 are displayed onscreen, e.g., as green or red dots 387-394 correspondingly (step S448). If imaging is complete (step S450), the subprocedure halts. Otherwise, if the adjusting is still being made (step S450), return is made to step S432.

Also concurrently with step S426 of subprocedure main 420, the displacement tracking subprocedure 440 checks for when the box-span threshold $T_{BS}$ is met (step S452). Upon being met (step S452), an ablation monitoring subprocedure 450 is launched, and, in the current subprocedure 440, each of a series of push pulses 136 is produced (step S454). The pulses 136 of the series may be focused on a particular site 344, or on a group of sites, and may be repetitive over that group. Each push pulse 136 generates a respective shear wave originating from the site of the pulse (step S456). The consequent body tissue displacement, for each push pulse 136, is tracked by lateral location, and the tracking results are stored (step S458). If tracking is to continue (step S460), return is made to the threshold checking step S452. Subprocedure 450 updates a stiffness map and, based on the map, distinguishes zones 304, 312 in real time. In particular, the tissue displacements stored in step S458 are utilized to derive a shear stiffness map of the imaging zone 324 (step S460). The map is used to spatially identify the current borders between ablated body tissue and a transition zone, and between the transition zone and normal, non-treated body tissue (step S462). If this real-time monitoring is to continue (step S464), return is made to step S460.

These borders can be visually monitored by the physician in controlling, or stopping, the ablation procedure, thereby enabling sufficient ablation without excess damage to body tissue 316. Lines representing the borders can be graphically depicted onscreen, or the borders can be surmised by the physician based on a displayed, dynamically-updated color-coded rendition of the stiffness values in the map.

An ultrasound exposure safety processor is configured for spatially relating respective definitions of an imaging zone, and an extended dead-tissue zone that includes both a dead-tissue zone and a surrounding margin. Based on whether a push pulse focus is to be within the extended dead-tissue zone, the processor automatically decides as to a level of acoustic power with which the pulse is to be produced. If the pulse focus is to be within the extended dead-tissue zone, the pulse may be produced with an MI, a TI, and/or an $I_{SPTA}$ that exceeds respectively 1.9, 6.0 and 720 milliwatts per square centimeter. The imaging zone may be definable interactively so as to dynamically trigger the deciding and the producing, with optimal push pulse settings being dynamically derived automatically, without the need for user intervention. A display of multiple push pulse sites allows user manipulation of spatial definition indicia to dynamically control displacement tracking.

The proposed methodology can advantageously be applied clinically in cardiac and non-cardiac treatment or examination. Clinical application can be made to examination or monitoring of bodily tissue such as the liver, prostate, and myocardium, where local tissue stiffness will be elevated by therapy treatment, such as heat based RF ablation, HIFU and microwave ablation, or for staging a tumor pre-surgery.

While the invention has been illustrated and described in detail in the drawings and foregoing description, such illustration and description are to be considered illustrative or exemplary and not restrictive; the invention is not limited to the disclosed embodiments.

For example, the shear stiffness map may be displayed as an overlay on the B-mode image supplemented with push pulse sites, or may be displayed separately, alongside, overlaying a separate B-mode image. As another example, the visualization of extended dead-tissue zone, the imaging zone, pulse site symbols, and ultrasound image may be implemented as three-dimensional.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. A medical apparatus, comprising:
    an exposure safety processor configured to:
        receive imaging data from a subject;
        assess the imaging data to define an extended target dead tissue zone and a shear wave elastography imaging zone, wherein the extended target dead tissue zone comprises a treatment zone and a margin at least partially surrounding the treatment zone, and wherein the shear wave elastography imaging zone defines a boundary for one or more push pulses;
        determine whether the shear wave elastography imaging zone is within the extended target dead tissue zone;
        initiate a push pulse having a first level of acoustic power not exceeding a diagnostic acoustic level to generate a first shear wave when the shear wave elastography imaging zone is determined to be outside of the extended target dead tissue zone, wherein the diagnostic acoustic level has at least one of a mechanical index equal to or less than 1.9, a thermal index equal to or less than 6, or a spatial-peak-temporal-average intensity equal to or less than 720 milliwatts per square centimeter; and
        initiate a push pulse having a second level of acoustic power that exceeds the diagnostic acoustic level to generate a second shear wave when the shear wave elastography imaging zone is determined to be within the extended target dead tissue zone, wherein the push pulse having the first level of acoustic power and the push pulse having the second level of acoustic power are included in the one or more push pulses.

2. The medical apparatus of claim 1, wherein the imaging data is ultrasound data.

3. The medical apparatus claim of 1, wherein the treatment zone comprises a tissue to be ablated, an ablated tissue, or a combination of the tissue to be ablated and the ablated tissue.

4. The medical apparatus of claim 3, wherein the tissue to be ablated or the ablated tissue comprise tissue selected from a group consisting of liver, prostate, and myocardium.

5. The medical apparatus of claim 1, wherein the second level of acoustic power exceeds a pre-determined threshold when the shear wave elastography imaging zone is determined to be within the extended target dead tissue zone.

6. The medical apparatus of claim 1, wherein the second level of acoustic power exceeds a pre-determined threshold when the shear wave elastography imaging zone is determined to be within the margin.

7. The medical apparatus of claim 1, wherein the second level of acoustic power exceeds a pre-determined threshold when the shear wave elastography imaging zone is determined to be within the treatment zone, the margin, ora combination of the treatment zone and the margin, wherein the second level of acoustic power in the treatment zone is greater than the second level of acoustic power in the margin.

8. The medical apparatus of claim 1, wherein the exposure safety processor is further configured to initiate tracking pulses along a beam formed by at least one of the push pulse of the first level of acoustic power or the push pulse of the second level of acoustic power.

9. The medical apparatus of claim 1, wherein the exposure safety processor is coupled to a user interface.

10. The medical apparatus of claim 9, wherein the user interface comprises a graphical display.

11. The medical apparatus of claim 10, wherein the exposure safety processor is further configured to display the extended target tissue zone and the shear wave elastography imaging zone on the graphical display.

12. The medical apparatus of claim 9, wherein the exposure safety processor is further configured to generate a stiffness map of the extended target dead tissue zone and the shear wave elastography imaging zone.

13. The medical apparatus of claim 12, wherein the stiffness map illustrates boundaries between the treatment zone, the margin, and the shear wave elastography imaging zone.

14. The medical apparatus of claim 1, wherein the imaging data comprises a tissue subject to a procedure selected from a group consisting of radiofrequency ablation, high-intensity frequency ultrasound, microwave ablation, and pre-tumor staging surgery.

\* \* \* \* \*